United States Patent
Ingold, Jr. et al.

(10) Patent No.: US 9,480,497 B2
(45) Date of Patent: Nov. 1, 2016

(54) SKIN NICKING DEVICE, METHOD AND ASSEMBLY

(75) Inventors: James E. Ingold, Jr., Hillsborough, NC (US); Thomas Vincent Casey, II, Troy, NY (US)

(73) Assignee: Angiodynamics, Inc., Latham, NY (US)

( * ) Notice: Subject to any disclaimer, the term of this patent is extended or adjusted under 35 U.S.C. 154(b) by 726 days.

(21) Appl. No.: 13/363,590

(22) Filed: Feb. 1, 2012

(65) Prior Publication Data

US 2013/0197558 A1     Aug. 1, 2013

(51) Int. Cl.
*A61B 17/34*     (2006.01)
*A61B 17/3209*     (2006.01)

(52) U.S. Cl.
CPC .......... *A61B 17/34* (2013.01); *A61B 17/32093* (2013.01); *A61B 17/3415* (2013.01); *A61B 2017/3492* (2013.01); *A61B 2090/036* (2016.02)

(58) Field of Classification Search
CPC ............ A61B 17/32; A61B 17/32093; A61B 17/3211; A61B 17/3494; A61B 2017/32113
USPC .......................... 606/167, 170, 172, 182, 185
See application file for complete search history.

(56) References Cited

U.S. PATENT DOCUMENTS

| | | | |
|---|---|---|---|
| 5,370,654 A * | 12/1994 | Abidin et al. | 606/182 |
| 5,843,108 A | 12/1998 | Samuels | |
| 6,019,771 A * | 2/2000 | Bennett et al. | 606/159 |
| 6,083,177 A * | 7/2000 | Kobren et al. | 600/564 |
| D472,318 S | 3/2003 | Solem | |
| 6,716,228 B2 | 4/2004 | Tal | |
| 7,341,596 B2 | 3/2008 | Heppler | |
| 2003/0204200 A1* | 10/2003 | Rufener | 606/172 |
| 2004/0133227 A1* | 7/2004 | Shang et al. | 606/182 |
| 2007/0288043 A1* | 12/2007 | Rehnke | A61B 1/313 606/170 |
| 2010/0140125 A1* | 6/2010 | Mathiasen | A61M 5/158 206/365 |
| 2011/0118759 A1 | 5/2011 | Teichman et al. | |
| 2013/0220671 A1* | 8/2013 | Fischbach | 174/163 R |

FOREIGN PATENT DOCUMENTS

| WO | WO 2005076943 | 8/2005 |
|---|---|---|
| WO | WO 2008036951 | 3/2008 |

* cited by examiner

*Primary Examiner* — Ashley Fishback
(74) *Attorney, Agent, or Firm* — Zachary F. Madonna

(57) ABSTRACT

A device, method and assembly for nicking skin is disclosed. The device includes a lumen is that is slideable over an introducer needle, and a blade at the end of the device. The device may include a shield for restricting advancement of the device during a skin nicking procedure. The device may also include a retractable blade or guard as a safety and nicking customization feature. A recess can also be shaped in the device for slideably attaching the device to an introducer needle hub.

13 Claims, 13 Drawing Sheets

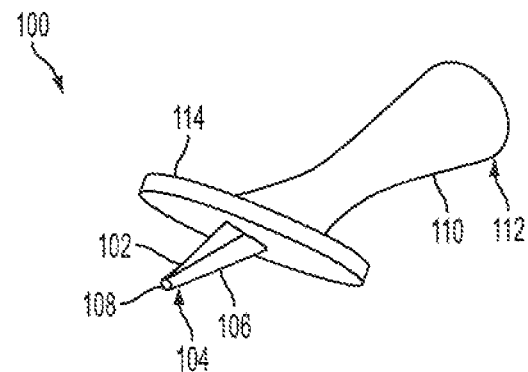
FIG. 2
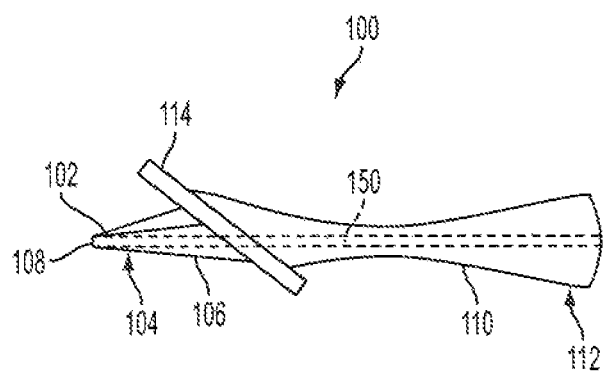
FIG. 3
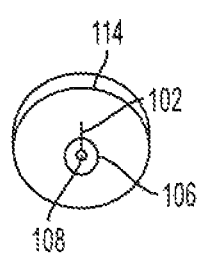 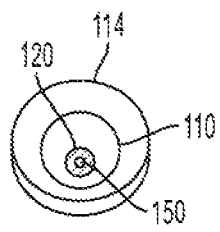
FIG. 4A          FIG. 4B

SKIN NICKING DEVICE, METHOD AND ASSEMBLY

TECHNICAL FIELD

The present invention relates generally to a device, method and assembly for nicking skin. More specifically, the invention relates to a skin nicking device that is slideable over an introducer needle.

BACKGROUND OF THE INVENTION

Elongate medical devices such as introducer sheaths are commonly used in medical procedures for gaining access to a subcutaneous site within a human body by providing a hollow pathway between the surface of the skin and the target site. For example, catheter insertion procedures such as peripherally inserted central catheter placement or midline catheter placement commonly utilize introducer sheaths for gaining access to the lumen of a blood vessel. A typical introducer sheath is made from a thin hollow plastic tubular structure with a hollow opening on the insertion or distal end and a hemostatic valve on the proximal end. Introducer sheaths come in a variety of shapes and sizes, and medical professionals typically select a shape and size corresponding to the type of procedure being performed and the access site being targeted. Introducer sheaths also include a dilator with a tapered distal end for accommodating a smooth transition as the sheath is advanced through a venipuncture site and into the lumen of the blood vessel. The introducer sheath and dilator are typically packaged together as a dilator sheath assembly.

FIGS. 1A-1E show an exemplary prior art technique for inserting a dilator sheath assembly into the blood vessel of a patient 10. A venipuncture is performed with a percutaneous introducer needle 50 by inserting the needle 50 into the skin 12 at an approximately 30-45 degree angle with the surface of the skin. The needle 50 is advanced through tissue 14 until the tip of the distal end 58 of the needle 50 enters the lumen of the target blood vessel 16. Detection of flashback indicates that the tip of the needle has entered the lumen of the blood vessel and that the tip of the needle 50 is properly positioned. As shown in FIG. 1B, once the needle is properly positioned with fluid access to the target blood vessel 16, a guide wire 60 can be inserted into the proximal end 52 of the needle, advanced to the distal end 58, advanced out of the needle tip and into the blood vessel 16. With the guide wire 60 positioned within the blood vessel 16, the needle 50 can be retracted off the guide wire 60, and access is maintained via the guide wire 60 as shown in FIG. 1C.

Now with reference to FIG. 1D, a small nick 18 is made in the skin 12 adjacent to the guide wire 60 at the venipuncture site using a scalpel 20. By nicking the skin, an opening 18 is created in the skin 12 for accommodating advancement of the dilator sheath assembly 22 or other elongate medical device over the guide wire 60 and into the blood vessel 16. Without nicking the skin, the medical professional performing the procedure may encounter significant resistance while attempting to advance the dilator sheath assembly 22 through the skin 12. Further, if the venipuncture site is too small, the opening 28 of the sheath 26 which coaxially surrounds the dilator 24 may curl back or "fish mouth" as the medical professional attempts to advance it through the skin 12, causing damage to the sheath 26 and possibly injury to the patient 10.

More generally, nicking the skin with a scalpel is common for procedures facilitating subcutaneous access and insertion of a variety of elongate medical devices. For example, certain angioplasty catheters for treatment for peripheral artery disease are designed for direct insertion into the arterial system without the need for a dilator sheath. Or, for example, for endovascular laser treatment, the skin may be nicked to facilitate advancing a procedure sheath or an optical fiber.

In the technique described above, medical professionals typically use a scalpel to nick the skin prior to inserting the elongate medical device, such as a dilator sheath assembly. However, problems arise when using a scalpel to perform the step of nicking the skin. For example, creating a small nick that is accurately close to the venipuncture site requires precise maneuvering of the scalpel to avoid damaging the guide wire. Medical professionals are warned against contacting the sharp side of the scalpel with the guide wire since it is fragile and can be easily damaged. A damaged guide wire may require removal from the patient or restarting the procedure with a new guide wire, further increasing risk to the patient. Further, it is difficult to consistently create a small nick in the skin of appropriate size. Skin nicks that are too small will not facilitate insertion of the elongate medical device. Conversely, excessively large nicks may cause unnecessary bleeding and scaring in the patient. Still further, including a scalpel as a separate component in an access kit requires more space in the kit and adds inefficiency to the procedure. Therefore, there is a need for an improved device, method and assembly for accurately, consistently and efficiently nicking the skin without risking damage to the guide wire, and while minimizing risk of injury to the patient.

SUMMARY

The present invention is directed to a device, method and assembly for nicking the skin using a device that is slideable over an introducer needle.

In one embodiment, the device for nicking skin includes an elongate member having a proximal portion and a distal portion, a lumen extending at least partially through the elongate member, where the lumen is configured to be slideable over an introducer needle, and a first blade disposed on the distal portion of the elongate member.

In another embodiment, a method for preparing skin for insertion of an elongate medical device includes providing an introducer needle having a proximal portion and a distal portion, and providing an elongate member having a proximal portion, a distal portion, and a lumen extending at least partially through the elongate member. The lumen is configured to be slideable over the introducer needle, and a first blade is disposed on the distal portion of the elongate member. The needle is advanced to a target site below a surface of the skin, and the elongate member is slid along the introducer needle from the proximal portion of the introducer needle towards the distal portion of the introducer needle to nick the skin. The needle is then removed from below the surface of the skin.

In another embodiment, an assembly for obtaining access to a site within a lumen of a blood vessel includes an introducer needle having a hub and a skin nicking device. The skin nicking device includes an elongate member having a proximal portion and a distal portion, where the proximal portion of the elongate member is slideably attachable to the hub, a lumen extends at least partially through the elongate member, the lumen is configured to be slideable over an introducer needle, and a first blade is disposed on the distal portion of the elongate member. The elongate member is coaxially loaded over the needle and attached to the hub.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 1A is a side view, partially cut away, of an introducer needle advanced into the lumen of a blood vessel; FIG. 1B is a side view, partially cut away, of a guide wire advanced into the lumen of a blood vessel; FIG. 1C is a side view, partially cut away, of a guide wire with access to the lumen of a blood vessel; FIG. 1D is a side view, partially cut away, of a scalpel nicking the skin; FIG. 1E is a side view, partially cut away, of a dilator sheath assembly being advanced over a guide wire;

FIG. 2 is a perspective view of a skin nicking device according to an exemplary embodiment of the present invention;

FIG. 3 is an side view of the skin nicking device shown in FIG. 2;

FIG. 4A is front view of the skin nicking device shown in FIG. 2; FIG. 4B is a back view of the skin nicking device shown in FIG. 2;

FIG. 5A is a side view, partially cut away, of the skin nicking device shown in FIG. 2 loaded over a needle and attached to a needle hub; FIG. 5B is a side view, partially cut away, of the skin nicking device shown in FIG. 2 advanced into the skin and forming a skin nick; FIG. 5C is a side view, partially cut away, of the skin nicking device being retracted from the surface of the skin;

FIG. 7A shows the device detached from a needle hub; FIG. 7B shows the device attached to a needle hub;

FIG. 12A shows the slider at P1 and the blade retracted in the device housing; FIG. 12B shows the slider at P2 and the exposed portion of the blade at height H1; FIG. 12C shows the slider at P3 and the exposed portion of the blade at height H2;

DETAILED DESCRIPTION OF THE INVENTION

Figure 1A:
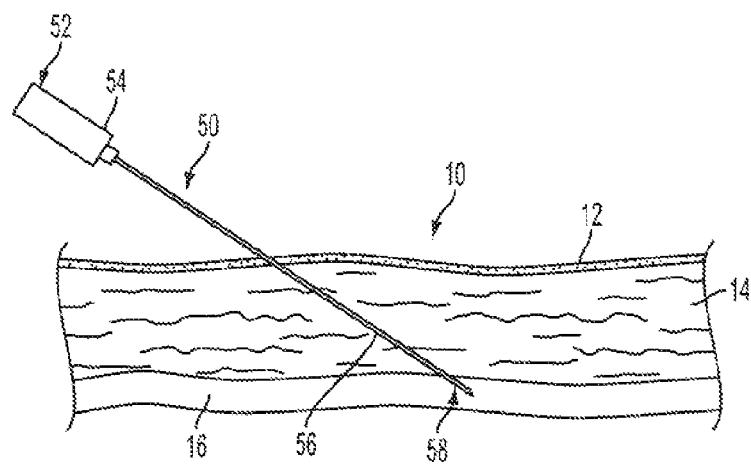
FIGS. 1A-1E illustrate a prior art technique for creating introducer sheath access to the lumen of a blood vessel.
Figure 1B:
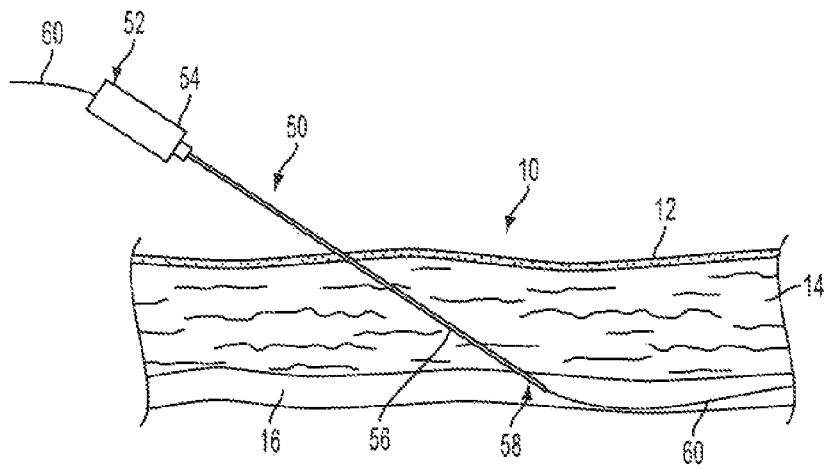
Figure 1C:
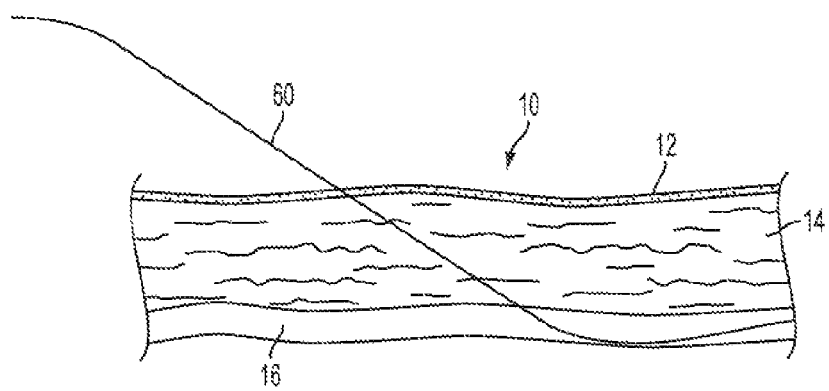
Figure 1D:
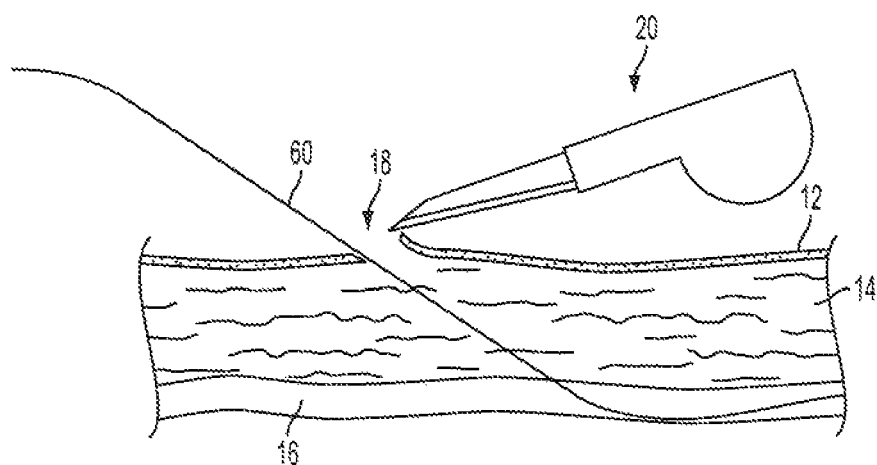
Figure 1E:
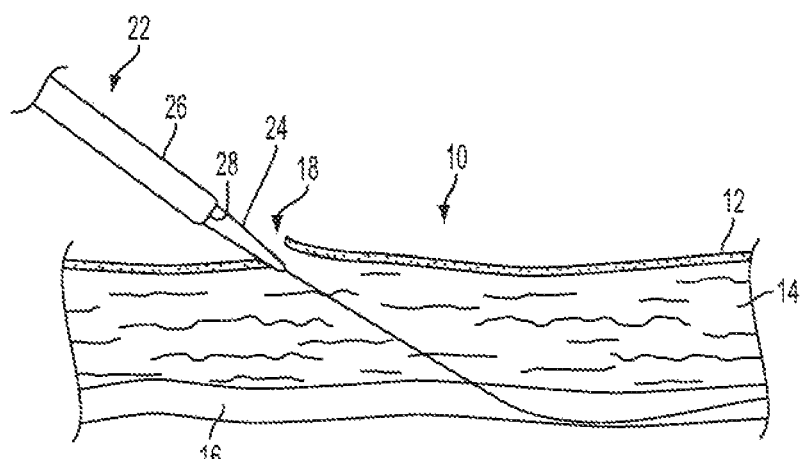
Figure 5A:
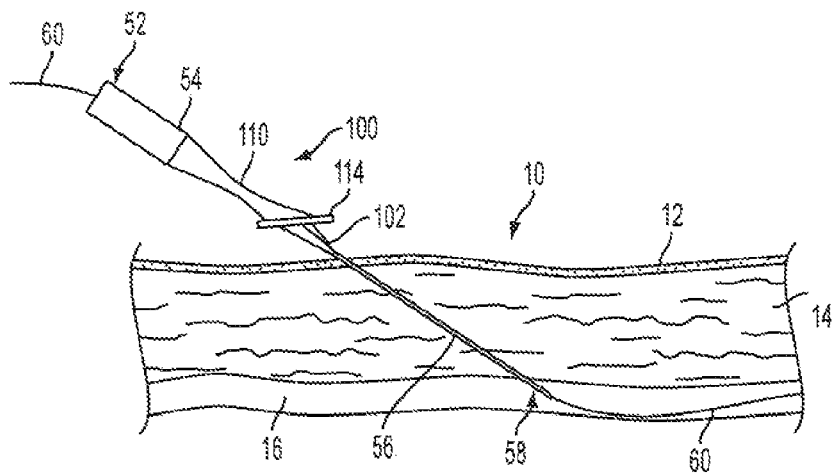
FIGS. 5A-5C show a technique for creating introducer sheath access to the lumen of a blood vessel according to an exemplary embodiment of the present invention.
Figure 5B:
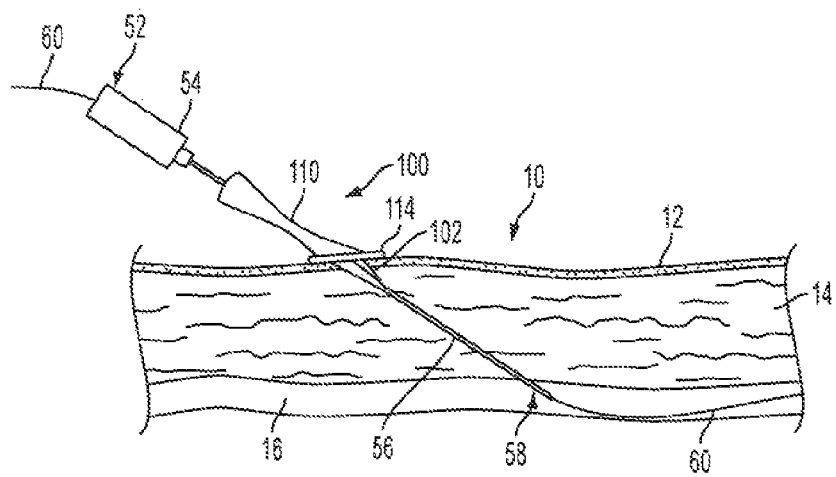
Figure 5C:
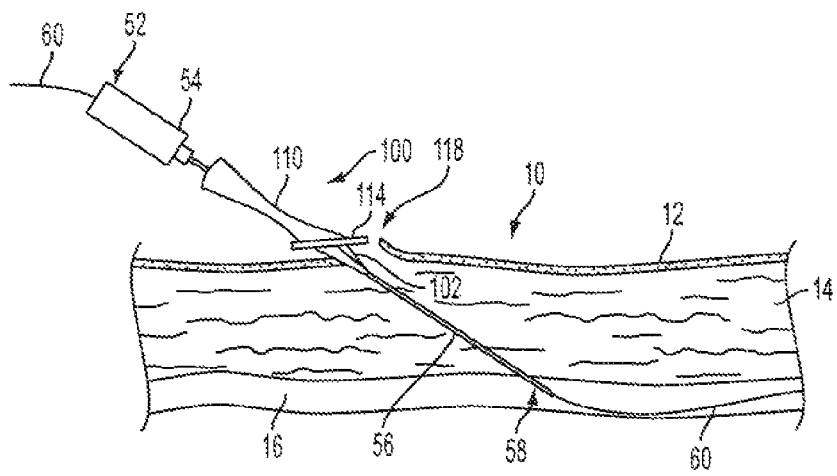

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a skin nicking device, method and assembly.

FIG. 2 shows a skin nicking device according to an exemplary embodiment of the present invention. The body of the skin nicking device 100 is generally an elongate member made of a medical grade material such as plastic. The outside of the device 100 has at least one blade 102 for creating a nick in the skin. As better illustrated in FIG. 3, a lumen 150 extends from the proximal end 112 to the distal end 104 of the device. The blade 102 is positioned on the distal portion 104 of the device, at or near the distal lumen opening 108 of the lumen 150. The blade 102 is exposed to the outer surface of the distal portion 104 of the device 100 so that as the device 100 is advanced distally over a guide wire, the blade will contact a skin surface and nick the skin. The distal portion 104 of the device 100 can taper distally 106 to facilitate the creation of an opening for a dilator sheath assembly. The proximal portion 112 of the device 100 can include concave or other ergonomic features 110 for improved tactile feedback for the medical professional operating the device. More than one blade can be positioned on the distal portion 104 of the device, for example two blades can be positioned in an opposing configuration or a "V" configuration.

To improve accuracy regarding the depth and length of the skin nick, a shield 114 can be positioned proximal to the blade 102 to limit how far the device 100 can be advanced into the skin. To accommodate the typical 30-45 degree angle of insertion for the introducer needle, the shield 114 can be angled within 30-45 degrees of the longitudinal axis of the lumen 150 so that once the blade 102 is fully advanced into the skin, the shield is flush with the outer surface of the skin. The blade can be made from a transparent medical grade material so that the shield does not block the view of the medical professional performing the procedure. An absorbent material can also be placed on the distal surface of the shield to absorb any blood that comes to the surface of the skin during the nicking procedure. The device 100 can be manufactured using manufacturing processes known in the art, for example molding separate plastic components and assembling the device using a snap-fit and/or ultrasonic welding process. The blade 102 can be made of a medical grade metal such as stainless steel or carbon steel.

FIGS. 4A and 4B show front and back views of skin nicking device 100 respectively. As shown in FIG. 4A, the blade 102 is positioned above the distal lumen opening 108 so that as the device is advanced over a needle shaft (e.g. 56, FIGS. 1A-1C and 5A-5C), the blade has enough separation to avoid contacting the needle shaft 56. FIG. 4B shows a recess 120 that can be formed in the proximal portion 112 of the device 100 for press fitting and attaching the device 110 onto a needle hub. Since the device 100 can be attached to a needle hub, the device can be offered to medical professionals as a pre-loaded assembly attached the introducer needle. Further, press fitting the device 100 with an introducer needle to provide a single assembly gives medical professionals the added efficiency of performing the venipuncture step and introducer needle retraction step without the need to handle the nicking device 100 separately. Alternatively, the recess can be formed in the needle hub with the proximal end of the device 100 shaped to press fit into the recess. Alternate methods known in the art of slidably attaching the two members can be also used.

Figure 6:
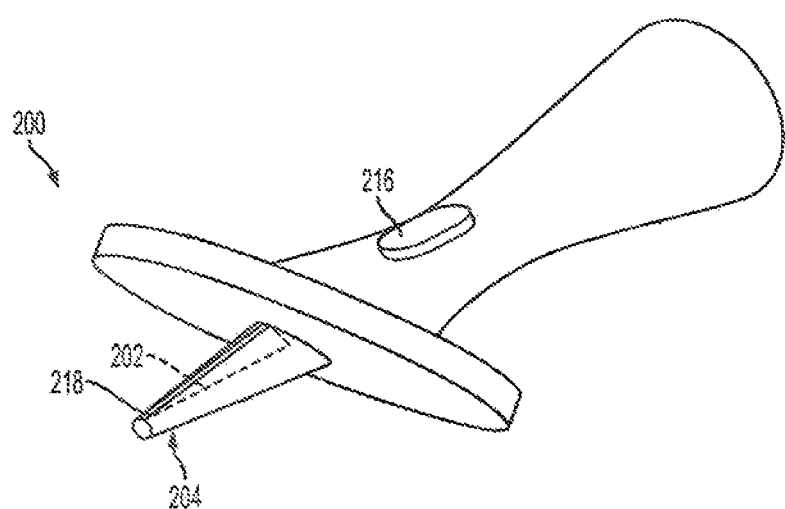
FIG. 6 is a perspective view of a skin nicking device with a deployable blade according to an exemplary embodiment of the present invention.

FIG. 6 shows a skin nicking device 200 according to an exemplary embodiment of the present invention. The distal portion 204 of the device 200 includes a housing 218 for housing the blade 202 below an outer surface of the device. A tactile feature such as a button 216 is included for deploying and exposing the blade 202 above the surface of the device. The distal end of the blade 202 can be hinged to an inner surface of the housing 218, and the blade 202 and button 216 can be connected to each other by a lever tensioned with springs for deploying the blade 202 when the button 216 is pressed down and returning the blade 202 to the housing 218 once the button is released.

Figure 7A:
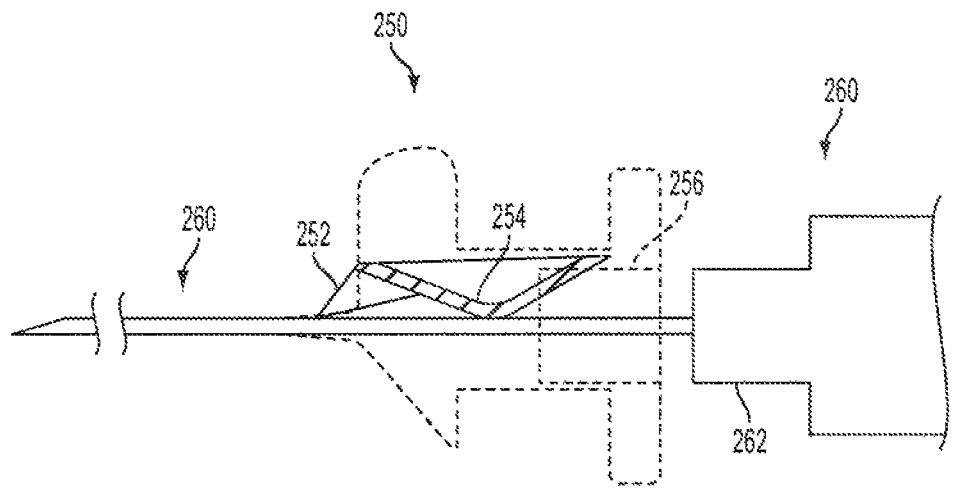
FIGS. 7A and 7B show side views, partially cut away, of a skin nicking device with a deployable blade according to an exemplary embodiment of the present invention.
Figure 7B:
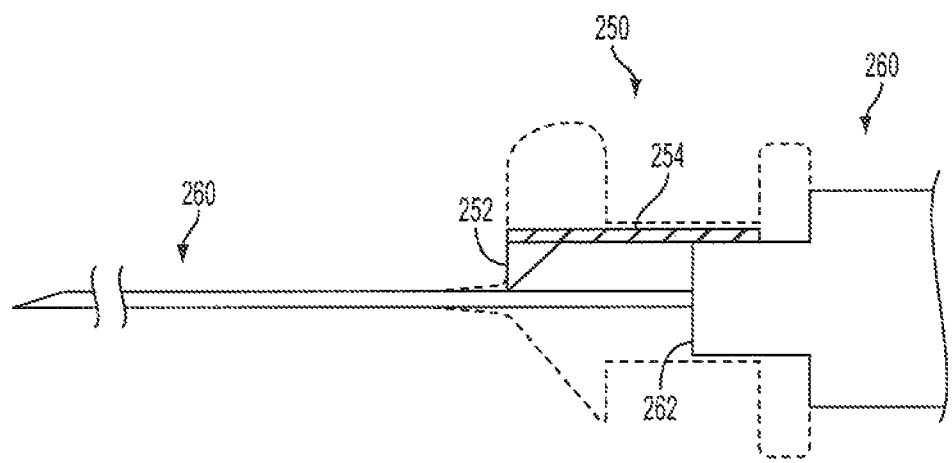

Alternatively, as shown in FIGS. 7A and 7B, a button or elastic element 254 can be configured to interact with the recess 256. With reference to FIG. 7A, the blade 252 is deployed from a housing while the device 250 is detached from the needle hub 262. The elastic element 254 is formed and positioned within the device so that in a detached state, the blade 252 is deployed to a pre-determined position for exposure outside the housing. Once the device 250 is connected to the needle hub 262, the edges of the needle hub 262 force the elastic element 254 to deform, safely storing the attached blade 252 within the housing. The elastic element can be for example a thin elongated metal or plastic band, and the mounting configuration can be customized based on the desired positioning of the blade. When a medical professional performs the venipuncture with the device 250 attached to the introducer needle 260 as an assembly, the blade 252 will be safely housed within the body of the device 250. Once the medical professional advances the device 250 off of the needle hub 262, the elastic element 254 expands, the blade 252 is deployed, and the skin nicking procedure can be performed. The device 250 can then be re-attached to the needle hub 262, deforming the elastic element 254 and housing the blade 252 for safe removal of the assembly.

Figure 8:
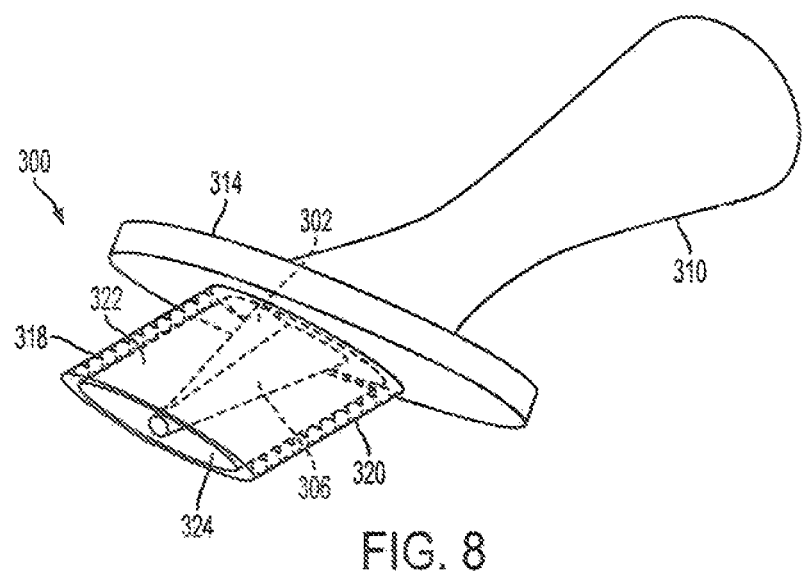
FIG. 8 is a perspective view of a skin nicking device with an elastic cover according to an exemplary embodiment of the present invention.

FIG. 8 shows a skin nicking device 300 according to an exemplary embodiment of the present invention, including a handle 310, a shield 314, a conical distal portion 306 and a retractable cover 322. The cover 322 coaxially surrounds the blade 302 and the conical distal portion 306. The cover has two elastic springs 318, 320, so that once the distal opening 324 of the cover 322 hits the skin, the cover 322 will retract proximally. Alternate types of elastic components can be used to prop the cover past the distal lumen opening 408 or the distal tip of the blade 402. The cover can be made of a transparent material such as a clear plastic membrane, so that the medical professional performing the skin nicking procedure can view the blade entering the skin.

Figure 9:
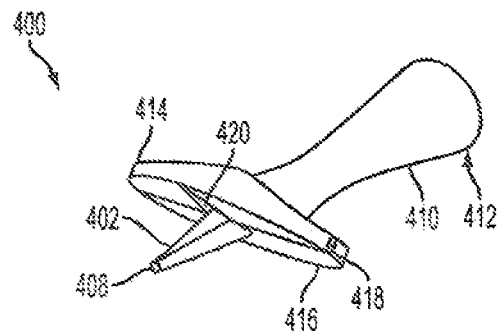
FIG. 9 is a perspective view of a skin nicking device with a hinged shield according to an exemplary embodiment of the present invention.
Figure 10:
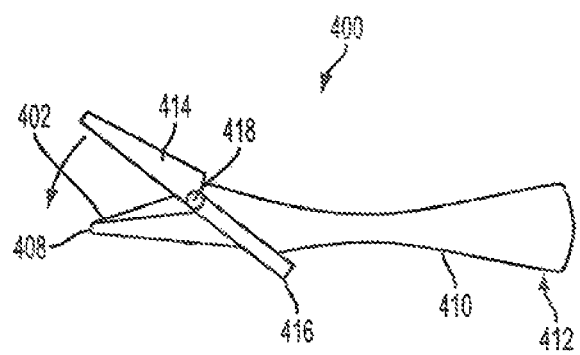
FIG. 10 is an side view of the skin nicking device shown in FIG. 9.

FIGS. 9 and 10 show a skin nicking device 400 according to an exemplary embodiment of the present invention, including a handle 410, a top 414 and bottom 416 shield member, a hinge 418 connecting the top 414 and bottom 416 shield member, a conical distal portion 306, and a distal lumen opening 408. The top shield member 414 has a cavity 420 for housing the blade 402, so that as the top shield member 414 is swung down in the direction illustrated in FIG. 10, the blade 402 will be safely housed and unexposed. For multi-blade embodiments, multiple cavities or larger cavities can be formed to accommodate the multi-blade configuration. Additionally, multiple shield members can be hinged and movable (e.g. closing a top and bottom shield member for a two blades in an opposing configuration), so that all blades are housed in a multi-blade embodiment. The proximal end 412 could also include a recess for attaching the device to a needle hub. Thus, the device 400 can be pre-loaded onto an introducer needle with the top shield member closed so that the medical professional can safely handle the assembly without the blade exposed.

Figure 11:
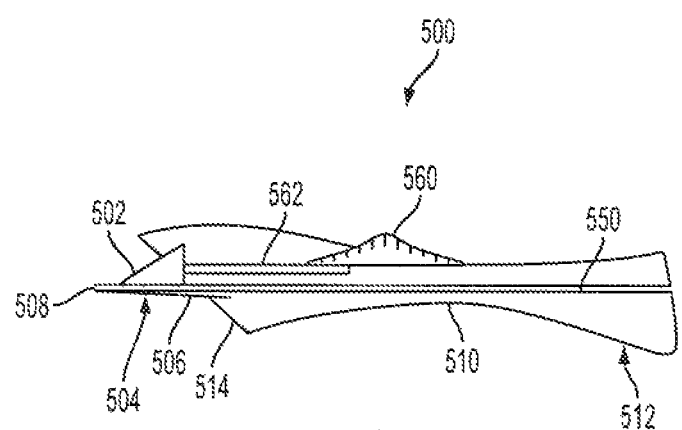
FIG. 11 is an side view, partially cut away, of a skin nicking device with a retractable blade according to an exemplary embodiment of the present invention.
Figure 12A:
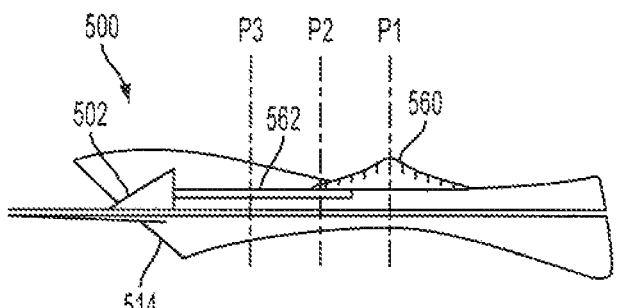
FIGS. 12A-12C show the relationship between the position of the blade and the height of the exposed portion of the blade.
Figure 12B:
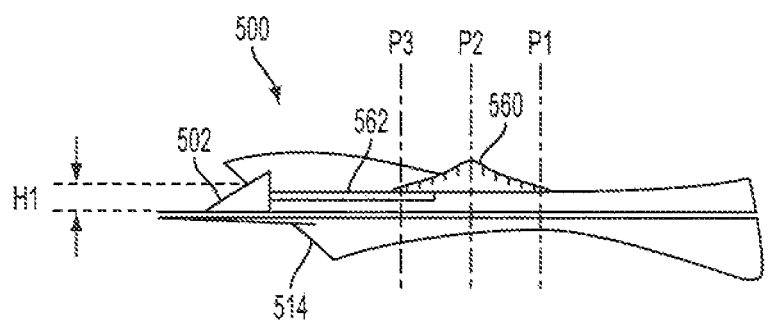
Figure 12C:
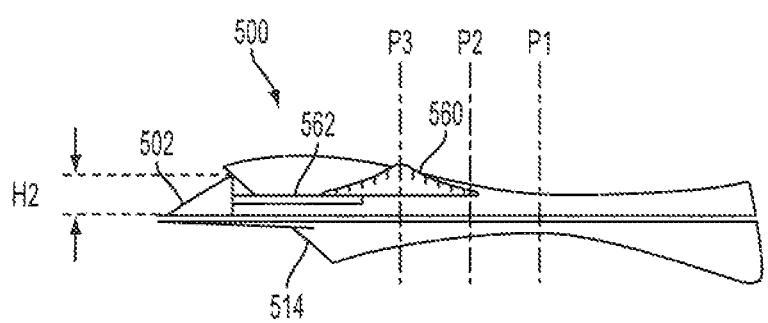

FIG. 11 shows a skin nicking device 500 according to an exemplary embodiment of the present invention, including a proximal portion 512, a distal portion 504, a handle 510, a tactile slideable button 560, an extension arm 562, a blade 502, a lumen 550, a distal lumen opening 508, a tapered portion 506 and a shield 514. The blade 502 is connected to the slideable button 560 by the extension arm 562. Referring now to FIGS. 12A-12C, the slideable button 560 can limited to a range that allows the blade 502 to be housed, partially exposed, or fully exposed. With the shield 514 angled to accommodate the angled entry of the introducer needle into the venipuncture site, the nicking device 500 has the added advantage of being able to customize the height and depth of the nick, depending on how far distally the blade 502 is deployed. For example, in FIG. 12A, the button 560 is in position P1, and the blade 502 is unexposed and safely housed within the body of the device 100. In FIG. 12B, the button 560 is slid distally to position P2, and the blade 502 is now partially exposed to height H1. In FIG. 12C, the button 560 is slid to an end range of position P3, fully exposing the blade 502 to height H2, wherein the lumen 550 extends distally to at least a plane perpendicular to a longitudinal axis of the lumen 550, wherein the plane includes a point on a distal tip of the blade 502. As illustrated in FIGS. 12B and 12C, the medical professional can customize the size of the skin nick by sliding the button 560 between positions P1 and P3. The blade shape can also be customized (e.g. square or circular) to create various customization effects as the blade is distally deployed from the device housing. Further, multiple buttons can be connected to multiple blades surrounding the lumen so that the medical professional has various deployment options depending on the patient's anatomy and the procedure being performed.

Figure 13:
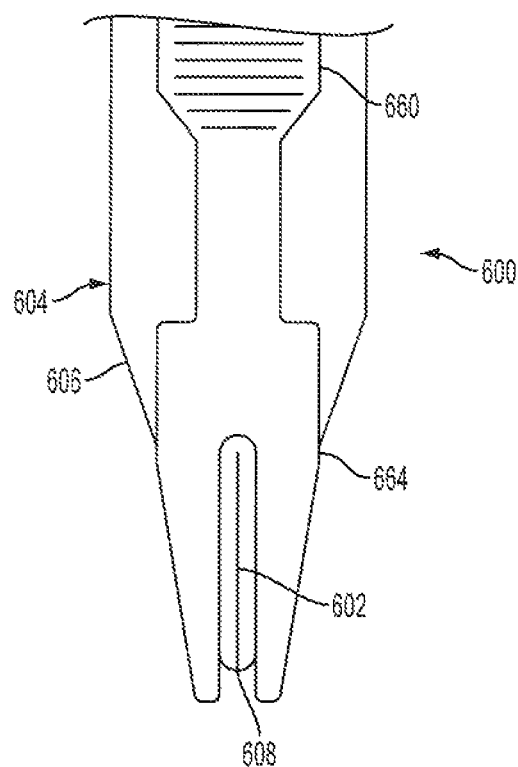
FIG. 13 is a top view of a skin nicking device with a retractable shield according to an exemplary embodiment of the present invention.
Figure 14:
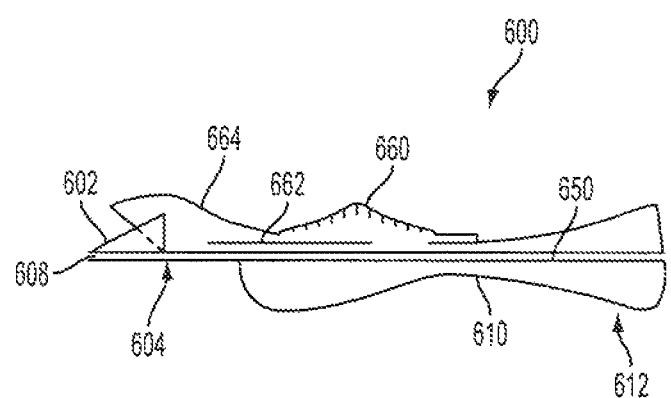
FIG. 14 is a side view, partially cut away, of the skin nicking device shown in FIG. 13.

Alternatively, as shown in the exemplary embodiment in FIGS. 13 and 14, the shield 664 can be slideably attached to the body of the device 600 by a track 662, so that as the shield 64 is retracted proximally, the blade 608 is revealed. As shown in FIG. 600, the device features a slideable button 660 attached to the shield 664, a blade fixed to the distal portion 604 of the device 600, a proximal portion 612 with an ergonomic feature 610, a lumen 650, and a distal lumen opening 608. Following the same principals illustrated in FIGS. 12A-12C, since the distal surface of the shield 664 is angled acutely with respect to the longitudinal axis of the device, as the shield 664 is retracted proximally, the height of the exposed portion of the blade increases. Thus, medical professionals can use the slideable button 660 to both customize the size of the nick and house the blade 602 for safe handling.

Figure 15:
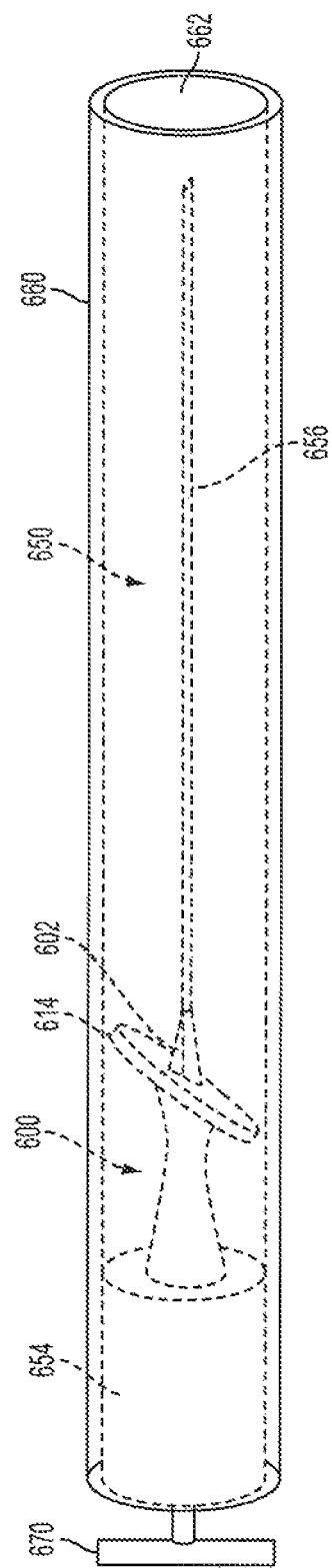
FIG. 15 is a side perspective view of an introducer needle and skin nicking device assembly packaged in a safety guard.

FIG. 15 shows an introducer needle 650 and nicking device 600 as a pre-loaded assembly packaged within a safety cover 660. As previously mentioned, the introducer needle 650 and nicking device 600 can be combined as an assembly, with the nicking device 600 coaxially pre-loaded and attached to the needle hub via a recess in the proximal end of the nicking device. For safe storage and transport, the assembly can include a clear safety cover 660 that is designed to fit the needle hub 654 with clearance for the blade 602 and the shield 614 on the nicking device 600. A separate grasping element 670 can be connected to the hub 654 for removing the safety cover 660.

Figure 16:
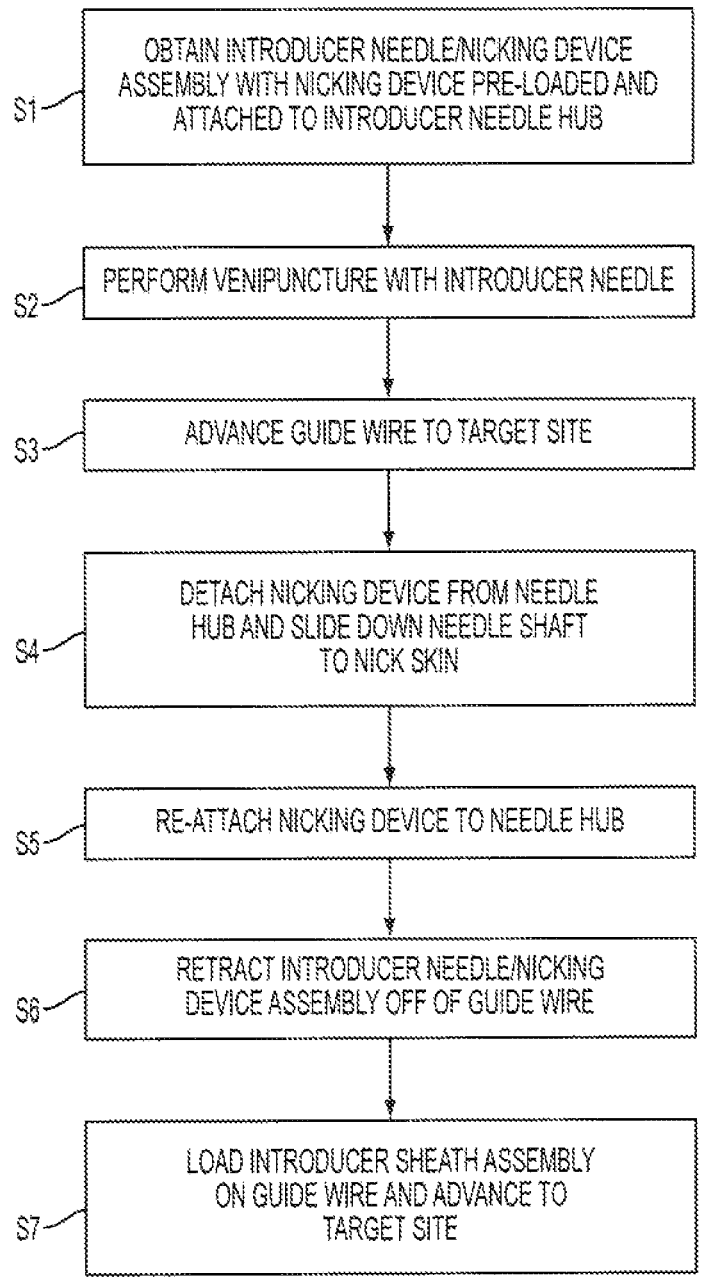
FIG. 16 is a diagram of a method for preparing skin for insertion of an introducer sheath.

When the nicking device is obtained by medical professionals as an assembly, a method of preparing the puncture site for insertion of the dilator sheath assembly or other elongate medical device can be efficiently and accurately executed as diagramed in FIG. 16. First, the introducer needle/nicking device assembly is obtained S1 as shown for example in FIG. 15, With the nicking device safely secured to a hub of the needle, the venipuncture is performed S2, and the guide wire is advanced through the needle lumen to the target site S3 within the blood vessel. With the nicking device readily accessible and attached to the needle hub, the nicking device can be advanced distally by sliding it along the shaft 656 of the needle down to the skin, creating a nick S4. If the nicking device had a safety or customization feature such as a hinged shield cover or a retractable blade, the medical professional can expose and prepare the blade for nicking prior to advancing the device down to the skin. Alternatively, for retractable embodiments, the device can be advanced to the surface of the skin, and the blade can be deployed once the shield is flush with the skin, stabilizing the skin during the nicking procedure. Once the nick is created, the nicking device can be reattached to the needle hub S6, and the medical professional can remove the entire assembly by simply retracting the needle off of the guide wire. If the device had a safety cover or retractable blade, the blade can be housed prior to disposal of the assembly. With the skin nicked at the venipuncture site, the dilator sheath assembly can be loaded over the guide wire and advanced to the lumen of the target blood vessel.

What is claimed is:

1. A device for nicking skin, the device comprising:
    an elongate member having a proximal portion and a distal portion,
    a lumen extending entirely through the elongate member from the proximal portion of the elongate member to the distal portion of the elongate member, wherein the lumen is configured to be coaxially loaded and slidable over an introducer needle, the introducer needle comprising a hub with a proximal portion and a distal portion and a needle extending from the hub, wherein the proximal portion of the elongate member is coaxially loaded over the needle and attachable to the distal portion of the hub; and
    a first blade slidably attached to the distal portion of the elongate member, wherein the lumen extends distally to at least a plane perpendicular to a longitudinal axis of the lumen, wherein the plane includes a point on a distal tip of the first blade.

2. The device of claim 1 further comprising:
    a shield extending away from the longitudinal axis, disposed proximate to a distal portion of the first blade.

3. The device of claim 2, wherein an angle between a distal surface of the shield and the longitudinal axis is between 15 and 70 degrees.

4. The device of claim 2, wherein the shield comprises a transparent material.

5. The device of claim 2, wherein the shield comprises a hinge and a cavity for housing the first blade.

6. The device of claim 1 further comprising:
    a shield extending away from the longitudinal axis,
    wherein the shield is slidably attached to the elongate member, and
    wherein the shield includes a cavity for housing at least a portion of the first blade.

7. The device of claim 6 further comprising:
    an adjustment member connected to the shield and configured for restricting a range of movement of the shield.

8. The device of claim 1, wherein the distal portion of the elongate member tapers distally.

9. The device of claim 1, further comprising:
    a tactile member for deploying the first blade from a housing below an outer surface of the distal portion of the elongate member.

10. The device of claim 1 further comprising:
    a cover comprising a proximal cover portion, a distal cover portion, and at least one elastic member,
    wherein the cover coaxially surrounds at least a portion of the first blade, and
    wherein the distal cover portion extends at least distally to a plane including a distal end of the first blade.

11. A method for preparing skin for insertion of an elongate medical device, the method comprising:
    placing at a target site:
        an introducer needle having a proximal portion, a distal portion, and a hub at the proximal portion of the introducer needle, the hub having a proximal portion and a distal portion, and
        an elongate member having a proximal portion and a distal portion, a lumen extending entirely through the elongate member from the proximal portion of the elongate member to the distal portion of the elongate member, wherein the lumen is configured to be coaxially loaded and slidable over the introducer needle, and a first blade disposed on the distal portion of the elongate member, wherein the lumen extends distally to at least a plane perpendicular to the longitudinal axis of the lumen, wherein the plane includes a point on a distal tip of the first blade;
    advancing the introducer needle to the target site below a surface of the skin;
    attaching the proximal portion of the elongate member to the distal portion of the introducer needle hub;
    disconnecting the elongate member from the introducer needle and sliding the elongate member along the introducer needle from the proximal portion of the introducer needle towards the distal portion of the introducer needle and nicking the skin;
    sliding the elongate member from the distal portion of the introducer needle towards the proximal portion of the introducer needle and reattaching the elongate member to the hub; and removing the introducer needle from below the surface of the skin.

12. An assembly for obtaining access to a site within a lumen of a blood vessel, the assembly comprising:
an introducer needle having a hub, the hub having a distal portion and a proximal portion and a needle extending from the hub; and
a skin nicking device including:
an elongate member having a proximal portion and a distal portion,
a lumen extending entirely through the proximal portion of the elongate member to the distal portion of the elongate member and sized to be slidable over the needle of the introducer needle such that the needle extends distally of the elongate member,
wherein the elongate member is coaxially loaded over the needle, the proximal portion of the elongate member being attachable to the distal end of the hub,
a first blade disposed on the distal portion of the elongate member, and
a shield comprising a hinge and a cavity for housing the first blade, the shield extending away from a longitudinal axis of the lumen d disposed proximate to a distal portion of the first blade.

13. The assembly of claim 12, wherein an angle between a distal surface of the shield and the longitudinal axis of the lumen is between 15 and 70 degrees.

* * * * *